(12) United States Patent
Miller

(10) Patent No.: US 7,608,578 B2
(45) Date of Patent: *Oct. 27, 2009

(54) OBESITY CONTROLLING METHOD

(75) Inventor: Larry S. Miller, Bala Cynwyd, PA (US)

(73) Assignee: Temple University - Of the Commonwealth System of Higher Education, Philadelphia, PA (US)

(*) Notice: Subject to any disclaimer, the term of this patent is extended or adjusted under 35 U.S.C. 154(b) by 175 days.

This patent is subject to a terminal disclaimer.

(21) Appl. No.: 10/343,668

(22) PCT Filed: Aug. 9, 2001

(86) PCT No.: PCT/US01/24971

§ 371 (c)(1),
(2), (4) Date: Aug. 13, 2003

(87) PCT Pub. No.: WO02/13854

PCT Pub. Date: Feb. 21, 2002

(65) Prior Publication Data

US 2004/0009224 A1    Jan. 15, 2004

Related U.S. Application Data

(60) Provisional application No. 60/224,324, filed on Aug. 11, 2000.

(51) Int. Cl.
*A61K 38/39* (2006.01)
*A61F 2/00* (2006.01)

(52) U.S. Cl. .................. 514/2; 530/356; 623/23.65; 607/40

(58) Field of Classification Search .................. None
See application file for complete search history.

(56) References Cited

U.S. PATENT DOCUMENTS

| | | | |
|---|---|---|---|
| 3,924,003 A | 12/1975 | Ho et al. | |
| 3,949,073 A | 4/1976 | Daniels et al. | |
| 3,963,780 A | 6/1976 | Manning | |
| 3,968,247 A | 7/1976 | Ho et al. | |
| 4,211,765 A | 7/1980 | Johnson et al. | |
| 4,212,876 A | 7/1980 | Houlihan | |
| 4,424,208 A | 1/1984 | Wallace et al. | |
| 4,592,339 A | 6/1986 | Kuzmak et al. | |
| 4,626,539 A | 12/1986 | Aungst et al. | |
| 4,803,075 A * | 2/1989 | Wallace et al. | 424/423 |
| 5,223,425 A | 6/1993 | Flier et al. | |
| 5,234,454 A | 8/1993 | Bangs | |
| 5,250,053 A | 10/1993 | Snyder | |
| 5,322,697 A | 6/1994 | Meyer | |
| 5,355,897 A | 10/1994 | Pietrafitta et al. | |
| 5,372,807 A | 12/1994 | Poiani et al. | |
| 5,423,872 A | 6/1995 | Cigaina | |
| 5,474,565 A | 12/1995 | Trott | |
| 5,490,984 A | 2/1996 | Freed | |
| 5,571,116 A | 11/1996 | Bolanos et al. | |
| 5,603,950 A | 2/1997 | Ratjen et al. | |
| 5,667,778 A | 9/1997 | Atala | |
| 5,752,974 A | 5/1998 | Rhee | |
| 5,792,153 A | 8/1998 | Swain et al. | |
| 5,792,478 A | 8/1998 | Lawin | |
| 5,820,584 A | 10/1998 | Crabb | |
| 5,834,027 A | 11/1998 | Cardinale Fezler | |
| 5,868,760 A | 2/1999 | McGuckin | |
| 5,877,216 A | 3/1999 | Place et al. | |
| 5,912,229 A | 6/1999 | Thim et al. | |
| 5,938,668 A | 8/1999 | Scirica et al. | |
| 5,976,526 A | 11/1999 | Atala | |
| 6,044,846 A | 4/2000 | Edwards | |
| 6,060,053 A | 5/2000 | Atala | |
| 6,097,984 A | 8/2000 | Douglas | |
| 6,139,555 A | 10/2000 | Hart et al. | |
| 6,234,955 B1 | 5/2001 | Silverman et al. | |
| 6,238,335 B1 | 5/2001 | Silverman et al. | |
| 6,248,058 B1 | 6/2001 | Silverman et al. | |
| 6,251,063 B1 | 6/2001 | Silverman et al. | |
| 6,251,064 B1 | 6/2001 | Silverman et al. | |
| 6,358,197 B1 | 3/2002 | Silverman et al. | |

(Continued)

FOREIGN PATENT DOCUMENTS

EP    0 473 185    8/1991

(Continued)

OTHER PUBLICATIONS

Roggen et al. 'Adult Hypertrophic Pyloric Stenosis: Case Report and Review' J. Clin. Pathol. 1998, vol. 51, pp. 479-480.*

(Continued)

*Primary Examiner*—Anish Gupta
(74) *Attorney, Agent, or Firm*—Wolf, Greenfield & Sacks, P.C.

(57) ABSTRACT

A method of controlling obesity by injecting bio-compatible bulking material into the pyloric sphincter area of the stomach. The injection of this material bulks the pyloric sphincter, retarding stomach emptying and producing a feeling of satiation in the patient. The method may be supplemental and augmented by inducing flaccid paralysis of the stomach by injecting botulinum toxin into the muscle tissue of the antrum or fundus of the stomach.

8 Claims, No Drawings

U.S. PATENT DOCUMENTS

| | | |
|---|---|---|
| 6,398,795 B1 | 6/2002 | McAlister et al. |
| 6,405,732 B1 | 6/2002 | Edwards et al. |
| 6,428,548 B1 | 8/2002 | Durgin et al. |
| 6,494,888 B1 | 12/2002 | Laufer |
| 6,530,878 B2 | 3/2003 | Silverman et al. |
| 6,533,717 B2 | 3/2003 | Silverman et al. |
| 6,537,314 B2 | 3/2003 | Langberg et al. |
| 6,540,789 B1 * | 4/2003 | Silverman et al. ........ 623/23.65 |
| 6,558,400 B2 * | 5/2003 | Deem et al. .................. 606/151 |
| 6,562,034 B2 | 5/2003 | Edwards et al. |
| 6,572,627 B2 | 6/2003 | Gabbay |
| 6,572,629 B2 | 6/2003 | Kalloo |
| 6,575,896 B2 | 6/2003 | Silverman et al. |
| 6,589,238 B2 | 7/2003 | Edwards et al. |
| 6,591,838 B2 | 7/2003 | Durgin |
| 6,592,596 B1 | 7/2003 | Geitz |
| 6,595,909 B2 | 7/2003 | Silverman et al. |
| 6,595,910 B2 | 7/2003 | Silverman et al. |
| 6,600,953 B2 | 7/2003 | Flesler et al. |
| 6,605,294 B2 | 8/2003 | Sawhney |
| 6,613,047 B2 | 9/2003 | Edwards |
| 6,663,639 B1 | 12/2003 | Laufer |
| 6,675,809 B2 | 1/2004 | Stack et al. |
| 6,695,764 B2 | 2/2004 | Silverman et al. |
| 6,712,814 B2 | 3/2004 | Edwards et al. |
| 6,716,222 B2 | 4/2004 | McAlister et al. |
| 6,736,828 B1 | 5/2004 | Adams et al. |
| 6,740,082 B2 | 5/2004 | Shadduck |
| 6,740,121 B2 | 5/2004 | Geitz |
| 6,773,440 B2 | 8/2004 | Gannoe |
| 6,773,441 B1 | 8/2004 | Laufer |
| 6,802,841 B2 | 10/2004 | Utley et al. |
| 6,802,868 B2 * | 10/2004 | Silverman et al. ........ 623/23.65 |
| 6,835,199 B2 | 12/2004 | McGuckin et al. |
| 6,835,200 B2 | 12/2004 | Laufer et al. |
| 6,846,312 B2 | 1/2005 | Edwards et al. |
| 6,866,663 B2 | 3/2005 | Edwards et al. |
| 6,895,258 B1 | 5/2005 | Scherzer et al. |
| 6,901,295 B2 | 5/2005 | Sharma |
| 6,916,332 B2 | 7/2005 | Adams |
| 6,944,570 B2 | 9/2005 | Neeser et al. |
| 6,955,643 B2 | 10/2005 | Gellman |
| 6,971,395 B2 | 12/2005 | Edwards et al. |
| 6,986,737 B2 | 1/2006 | Suzuki et al. |
| 6,993,391 B2 | 1/2006 | Flesler et al. |
| 6,994,095 B2 | 2/2006 | Burnett |
| 6,997,931 B2 | 2/2006 | Sauer et al. |
| 7,037,315 B2 | 5/2006 | Sancoff et al. |
| 7,037,343 B2 | 5/2006 | Imran |
| 7,044,979 B2 * | 5/2006 | Silverman et al. ........ 623/23.65 |
| 7,152,607 B2 | 12/2006 | Stack et al. |
| 7,175,638 B2 | 2/2007 | Gannoe, et al. |
| 7,175,669 B2 | 2/2007 | Geitz |
| 7,201,757 B2 | 4/2007 | Knudson et al. |
| 7,220,284 B2 | 5/2007 | Kagan et al. |
| 7,238,191 B2 | 7/2007 | Bachmann |
| 7,239,912 B2 | 7/2007 | Dobak |
| 2001/0046518 A1 | 11/2001 | Sawhney |
| 2002/0022851 A1 | 2/2002 | Kalloo et al. |
| 2002/0055750 A1 | 5/2002 | Durgin et al. |
| 2002/0055757 A1 | 5/2002 | Torre et al. |
| 2002/0065523 A1 | 5/2002 | McAlister et al. |
| 2002/0082616 A1 | 6/2002 | McAlister et al. |
| 2002/0082621 A1 | 6/2002 | Schurr et al. |
| 2002/0091395 A1 | 7/2002 | Gabbay |
| 2002/0107530 A1 | 8/2002 | Sauer et al. |
| 2002/0139379 A1 | 10/2002 | Edwards et al. |
| 2002/0143346 A1 | 10/2002 | McGuckin, Jr. et al. |
| 2002/0161414 A1 | 10/2002 | Flesler et al. |
| 2002/0183768 A1 | 12/2002 | Deem et al. |
| 2002/0188354 A1 | 12/2002 | Peghini |
| 2002/0193816 A1 | 12/2002 | Laufer et al. |
| 2003/0014086 A1 | 1/2003 | Sharma |
| 2003/0024538 A1 | 2/2003 | Edwards et al. |
| 2003/0055442 A1 | 3/2003 | Laufer et al. |
| 2003/0078466 A1 | 4/2003 | Silverman |
| 2003/0109892 A1 | 6/2003 | Deem et al. |
| 2003/0120321 A1 | 6/2003 | Bumm |
| 2003/0135206 A1 | 7/2003 | Edwards et al. |
| 2003/0144708 A1 | 7/2003 | Starkebaum |
| 2003/0158601 A1 | 8/2003 | Silverman et al. |
| 2003/0161887 A1 | 8/2003 | Klein |
| 2003/0181958 A1 | 9/2003 | Dobak |
| 2003/0188755 A1 | 10/2003 | Milbocker |
| 2003/0195509 A1 | 10/2003 | Edwards et al. |
| 2003/0208209 A1 | 11/2003 | Gambale |
| 2003/0220660 A1 | 11/2003 | Kortenbach et al. |
| 2003/0233108 A1 | 12/2003 | Gellman et al. |
| 2003/0236536 A1 | 12/2003 | Grigoryants et al. |
| 2004/0006351 A1 | 1/2004 | Gannoe et al. |
| 2004/0009224 A1 | 1/2004 | Miller |
| 2004/0015201 A1 | 1/2004 | Greenstein |
| 2004/0019388 A1 | 1/2004 | Starkebaum |
| 2004/0030217 A1 | 2/2004 | Yeung |
| 2004/0037865 A1 | 2/2004 | Miller |
| 2004/0044376 A1 | 3/2004 | Flesler et al. |
| 2004/0082859 A1 | 4/2004 | Schaer |
| 2004/0082950 A1 | 4/2004 | Edwards et al. |
| 2004/0082963 A1 | 4/2004 | Gannoe et al. |
| 2004/0087976 A1 | 5/2004 | DeVries et al. |
| 2004/0089313 A1 | 5/2004 | Utley et al. |
| 2004/0092892 A1 | 5/2004 | Kagan et al. |
| 2004/0096514 A1 | 5/2004 | Vogel et al. |
| 2004/0116949 A1 | 6/2004 | Ewers et al. |
| 2004/0122470 A1 | 6/2004 | Deem et al. |
| 2004/0122526 A1 | 6/2004 | Imran |
| 2004/0133220 A1 | 7/2004 | Lashinski et al. |
| 2004/0138744 A1 | 7/2004 | Lashinski et al. |
| 2004/0147921 A1 | 7/2004 | Edwards et al. |
| 2004/0153146 A1 | 8/2004 | Lashinski et al. |
| 2004/0158263 A1 | 8/2004 | McAlister et al. |
| 2004/0162567 A9 | 8/2004 | Adams |
| 2004/0162568 A1 | 8/2004 | Saadat et al. |
| 2004/0167546 A1 | 8/2004 | Saadat et al. |
| 2004/0186502 A1 | 9/2004 | Sampson |
| 2004/0193190 A1 | 9/2004 | Liddicoat et al. |
| 2004/0193194 A1 | 9/2004 | Laufer et al. |
| 2004/0194790 A1 | 10/2004 | Laufer et al. |
| 2004/0204708 A1 | 10/2004 | Edwards et al. |
| 2004/0210243 A1 | 10/2004 | Gannoe et al. |
| 2004/0215180 A1 | 10/2004 | Starkebaum et al. |
| 2004/0225183 A1 | 11/2004 | Michlitsch et al. |
| 2004/0225305 A1 | 11/2004 | Ewers et al. |
| 2004/0236356 A1 | 11/2004 | Rioux et al. |
| 2004/0248188 A1 | 12/2004 | Sanders |
| 2004/0260316 A1 | 12/2004 | Knudson et al. |
| 2005/0024222 A1 | 2/2005 | Nelson |
| 2005/0033319 A1 | 2/2005 | Gambale et al. |
| 2005/0033320 A1 | 2/2005 | McGuckin et al. |
| 2005/0033331 A1 | 2/2005 | Burnett et al. |
| 2005/0033332 A1 | 2/2005 | Burnett |
| 2005/0049718 A1 | 3/2005 | Dann et al. |
| 2005/0055038 A1 | 3/2005 | Kelleher et al. |
| 2005/0055039 A1 | 3/2005 | Burnett et al. |
| 2005/0060030 A1 | 3/2005 | Lashinski et al. |
| 2005/0065536 A1 | 3/2005 | Ewers et al. |
| 2005/0075653 A1 | 4/2005 | Saadat et al. |
| 2005/0085829 A1 | 4/2005 | Kraemer et al. |
| 2005/0085923 A1 | 4/2005 | Levine et al. |
| 2005/0090837 A1 | 4/2005 | Sixto et al. |
| 2005/0090873 A1 | 4/2005 | Imran |
| 2005/0096750 A1 | 5/2005 | Kagan et al. |
| 2005/0119671 A1 | 6/2005 | Reydel et al. |
| 2005/0137643 A1 | 6/2005 | Mintchev |

| | | | |
|---|---|---|---|
| 2005/0143760 | A1 | 6/2005 | Imran |
| 2005/0149067 | A1 | 7/2005 | Takemoto et al. |
| 2005/0149072 | A1 | 7/2005 | DeVries et al. |
| 2005/0149200 | A1 | 7/2005 | Silverman et al. |
| 2005/0154405 | A1 | 7/2005 | Kraemer et al. |
| 2005/0159743 | A1 | 7/2005 | Edwards et al. |
| 2005/0177176 | A1 | 8/2005 | Gerbi et al. |
| 2005/0192614 | A1 | 9/2005 | Binmoeller |
| 2005/0222492 | A1 | 10/2005 | Adams |
| 2005/0246037 | A1 | 11/2005 | Starkebaum |
| 2005/0267499 | A1 | 12/2005 | Stack et al. |
| 2006/0020278 | A1 | 1/2006 | Burnett et al. |
| 2006/0264983 | A1 | 11/2006 | Holsten et al. |
| 2006/0276812 | A1 | 12/2006 | Hill et al. |
| 2006/0282087 | A1 | 12/2006 | Binmoeller |
| 2007/0032702 | A1 | 2/2007 | Ortiz |
| 2007/0032800 | A1 | 2/2007 | Ortiz et al. |
| 2007/0129735 | A1 | 6/2007 | Filipi et al. |
| 2007/0129738 | A1 | 6/2007 | Kraemer et al. |
| 2007/0167963 | A1 | 7/2007 | Deem et al. |

FOREIGN PATENT DOCUMENTS

| | | |
|---|---|---|
| EP | 0 471 217 | 2/2002 |
| GB | 1174814 | 12/1969 |
| JP | 05255097 | 1/1992 |
| WO | WO 00/33908 | 6/2000 |
| WO | WO 00/35373 | 6/2000 |
| WO | WO 01/26588 A2 | 4/2001 |
| WO | WO 03/094785 | 11/2003 |
| WO | WO 2004/075974 | 9/2004 |
| WO | WO 2005/011463 A2 | 2/2005 |
| WO | WO 2005/011519 A2 | 2/2005 |
| WO | WO 2005/020802 A2 | 3/2005 |
| WO | WO 2007/019268 | 2/2007 |

OTHER PUBLICATIONS

Gui et al. Botulinum Toxin Injected in the Gastric Wall Reduces Body Weight and Food Intake in Rats. Aliment Pharmacol. Ther. 2000, 14; 829-834.*

M. B. Tchetgen, M. G. Sanda, J. E. Montie, G. J. Faerber, 'Collagen Injection for the Treatment of After Cystecomy and Orthotopic Neobladder Reconstruction in Women', Jan. 2000, vol. 163, p. 212-214.

P.J. Tschopp, T. W. James, A. Spekkens, L. Lohfeld, 'Collagen Injections for Urinary Stress Incontinence in a Small Urban Urology Practice: Time to Failure Analysis of 77 Cases', Sep. 1999, vol. 162, pp. 779-783.

Joseph Ortenberg, MD, 'Endoscopic Treatment of Vesicoureteral Reflux in Children', Feb. 1998, vol. 25, No. 1, pp. 151-156.

J. Christian Winters, MD, R. Appell, MD, 'Periurethal Injection of Collagen in the Treatment of Intrinsic Sphineteric Deficiency in the Female Patient', Aug. 1995, vol. 22, No. 3, pp. 673-678.

D. Kumar, M. J. Benson, J. E. Bland, (The British Journal of Surgery) 'Glutaraldehyde Cross-linked In The Treatment of Faecal Incontinence', Jul. 1998, vol. 85(7), pp. 978-979.

Yao et al., "Retrograde Gastric Pacing Reduces Food Intake and Delays Gastric Emptying In Humans: A Potential Therapy for Obesity?", Dig Dis Sci. Sep. 2005;50(9):1569-75.

Davis et al., "Closing the Pylorus Decreases The Size of Large Meals in the Rat", Physiol Behav. Jan. 1998;63(2):191-6.

Spaulding, Laurie, "Treatment of Dilated Gastrojejunostomy with Sclerotherapy", Obesity Surgery, 13, 254-257.

Sugerman, Harvey, "Bariatric Surgery for Severe Obesity", Journal of the Association for Academic Minority Physicians, vol. 12, No. 3, Jul. 2001, pp. 129-136.

Lundell, Lars, et al., "Measurement of Pouch Volume and Stoma Diameter After Gastroplasty", International Journal of Obesity (1987) 11, 169-174.

Miskowiak, J., et al., "Radiologic Findings and Weight Loss Following Gastroplasty for Morbid Obesity", Acta Radiologica Diagnosis 27 (1986) Fasc. 5, pp. 553-555.

Kirkpatrick, John R., et al., "Critical Determinants of a Successful Gastric Bypass: Reservoir Versus Stoma", vol. 77, No. 7, 1982, American Journal of Gastroenterology, pp. 464-466.

Schwartz, Richard W., "Gastric bypass revision: Lessons learned from 920 cases", Surgery, vol. 104, No. 4, pp. 806-812.

Soper, Robert T., "Gastric Bypass for Morbid Obesity in Children and Adolescents", Journal of Pediatric Surgery, vol. 10, No. 1, Feb. 1975, pp. 51-58.

Schweitzer, Michael, "Endoscopic Intraluminal Suture Plication of the Gastric Pouch and Stoma in Postoperative Roux-en-Y Gastric Bypass Patients", Journal of Laparoendoscopic & Advanced Surgical Techniques, vol. 14, No. 4, 2004, pp. 223-226.

Sarna, S.K., et al. "Gastric Pacemakers", Gastroenterology 70:226-231, 1976, Vol. 70, No. 2.

Xiaohong Xu, et al., "Pyloric Electrical Stimulation Reduces Food Intake by Inhibiting Gastric Motility in Dogs", Gastroenterology 2005; 128:43-50.

Keinke, Oliver, et al., Effect of Oleic Acid on Canine Gastroduodenal Motility, Pyloric Diameter and Gastric Emptying, Quarterly Journal of Experimental Physiology (1983) 68, 675-686.

Paraskevopoulos, J.A., et al. "Effect of Composition of Gastric Contents on Resistance to Emptying of Liquids from Stomachs in Humans", Digestive Diseases and Sciences, vol. 33, No. 8 (Aug. 1988), pp. 914-918.

Waitman, J.A., et al., "Obesity Surgery: Pros and Cons", J. Endocrinol. Invest. 25:925-928, 2002.

Dunn, Michael, "A Rare Cause of Pyloric Obstruction", The British Journal of Clinical Practice, vol. 29, No. 11, Nov. 1975.

Vassallo, C., et al., "Biliopancreatic Diversion with Transitory Gastric Restriction and Duodenal Bulb Preservation: 88 Patients since 1992", Obesity Surgery, 14, 2004, pp. 773-776.

Vassallo, C., et al., "Biliopancreatic Diversion with Transitory Gastroplasty Preserving Duodenal Bulb: 3 Years Experience", Obesity Surgery, 7, 1997, pp. 30-33.

Poulin, Eric, C., et al., "Correcting Reflux Laparoscopically", Can J. Gastroenterol vol. 12, No. 5 Jul./Aug. 1998, pp. 327-332.

Papavramidis, S., et al., "Vertical Gastroplasty with Artificial Pseudopylorus for Morbid Obesity Technique, Complications and Results in 100 Cases", Hellenic Journal of Gastroenterology 1996, 9(1) pp. 63-66.

International Search Report dated Oct. 30, 2001.

Cendron et al., "The Biological Behavior of Autologous Collagen Injected into the Rabbit Bladder" Journal of Urology, vol. 154, No. 2 Part 2, 1995, pp. 808-811, Abstract only.

Vicente, et al., "Enoscopic Injection of Teflon in Urinary Incontinence in Women", Journal D'Urologie, vol. 90. No. 1. 1984, pp. 35-38, Abstract only.

International Search Report.

* cited by examiner

OBESITY CONTROLLING METHOD

This application is a National Phase Application of International Patent Application No. PCT/US01/24971, filed Aug. 9, 2001, which claims priority of U.S. Provisional Application No. 60/224,324, filed Aug. 11, 2000.

The present invention relates to a method of controlling obesity by injecting bio-compatible bulking material into the pyloric sphincter area of the stomach. The injection of this material bulks the pyloric sphincter, retarding stomach emptying and producing a feeling of satiation in the patient.

BACKGROUND OF THE INVENTION

Obesity is one of the major causes of heart disease, lipid abnormalities, hypertension and osteoarthritis. Treatment of obesity has the potential to lower the risk of all of these diseases as well as improve the condition of patients who already suffer from such illnesses. In addition, it is well known that a large percentage of Americans and Europeans are considered to be obese based on height and weight ratios issued by the World Health Organization (WHO). These numbers in conjunction with the dangerous diseases affiliated with or caused by obesity indicate that there is a substantial need for effective treatment.

Current weight reduction programs usually include administration of systemic medications, which suppress the appetite or reduce the fat and/or sugar uptake of the digest track. However, systemic medications often display side effects some of which may be severe. Dietary changes that reduce caloric intake are also prescribed for the treatment of obesity, but such treatment requires rigorous compliance by the patient for effectiveness and is often ineffective as a result of non-compliance. In addition, surgery, which bypasses a portion of the stomach and/or the small intestine, is also used in the treatment of obesity. Surgical methods, however, are highly invasive and subject a patient to all the possible risks involved with major surgery including infection.

Safe and effective treatment is a long felt need in the treatment of obesity. Because of complications and/or ineffectiveness associated with current treatments a minimally invasive, effective treatment is preferred and is provided by the method of this invention.

SUMMARY OF THE INVENTION

The present invention provides a minimally invasive method for controlling obesity comprising injecting a bio-compatible bulking material submucosally or intramuscularly into the pyloric area of the stomach in an amount sufficient to cause the lumen of pylorus to narrow and slow gastric emptying.

DETAILED DESCRIPTION OF THE INVENTION

The entire disclosure of U.S. Patent Application No. 60/224,324, filed Aug. 11, 2000, is expressly incorporated by reference herein.

The invention is a method of treating obesity in which gastric emptying is slowed by narrowing the pyloric sphincter or pylorus. The invention comprises injecting a bio-compatible bulking material into the pyloric area of the stomach, preferably either submucosally or intramuscularly. By narrowing the pyloric region of the stomach, the stomach will fill more quickly and empty more slowly as a patient eats. The clinical effect of this treatment will be to increase the time the patient feels satiated after eating, therefore decreasing the need and desire to eat and reducing the caloric intake of the patient.

The pylorus can be caused to narrow by the injection of a bio-compatible bulking material into the mucosal or muscular area around the pylorus. Such an injection can be accomplished by a two step process wherein an endoscopy is performed to locate the pylorus and a needle is placed through the biopsy channel of the endoscope in order to inject the bulking material. Such an injection will increase the bulk of the pylorus and thus narrow the gastric outlet from the stomach to the start of the small intestines.

The bio-compatible bulking materials suitable for the present invention include collagen, fibrin and elastin as well as other naturally occurring and synthetically derived bio-compatible polymers. Certain polymers such as collagen or fibrin glue have been demonstrated to be well tolerated when injected into lumen in humans. In addition, such materials are commercially available. For instance, collagen may be purchased from FribroGen, Inc., Cohesion Technologies, Inc., Hydromer, Inc., and Bard, Inc., and fibrin glue may be purchased from Abbott Laboratories, Inc. Various other similar products for injection include, but are not limited to, Contigen® (Contigen is a registered trademark of the Collagen Corporation and is a protein composition for medical implants for relief of urinary tract disorders), Zyderm® (Zyderm is a registered trademark of the Collagen Corporation and is a protein composition for dermal implantation), Zyplast® (Zyplast is a registered trademark of the Collagen Corporation and is a collagen implant used for soft tissue augmentation), rh collagen, Dermalogen® (Dermalogen is a registered trademark of Collagenesis, Inc. and is injectable human tissue for treating wrinkles and scars), Autologen® (Autologen is a registered trademark of Autogenesis Technologies, Inc. and is processed collagen for implantation), and autologous fat.

Collagen for use in the present invention can be from several sources including porcine, bovine, or human. It can be either fibrillar or nonfibrillar. Collagen can be administered in aqueous solution form or in the denatured state as gelatin. In addition, it can be administered in either a crosslinked or a non-crosslinked form.

Although collagen is preferred as the bio-compatible bulking material to be injected into the pyloric muscle, other materials can be used. For instance, TEFLON paste (Teflon is a registered trademark of DuPont for fluoropolymer resins), synthetic polymeric hydrogels, glycoaminoglycans, proteoglycans, silicone microimplants, Durasphere® (Durasphere is a registered trademark of Advanced UroScience, Inc. and consists of biocompatible, implantable microspheres for local tissue augmentation), and microbeads suspended in biological fluid lubricants such as dextran have been demonstrated to be tolerated when injected into human lumen.

The amount of bio-compatible bulking material injected into the pyloric area of the stomach will be dependent of a variety of factors. For instance, the size of the individual, the severity of the individual's obesity, and the shape and distension of the pylorus will all be determinative in calculating the amount of bulking material injected. It is estimated that the opening of the pyloric sphincter can be reduced at least 10% and up to 90% by the instant invention.

The injection of collagen or fibrin glue into the pylorus is expected to last for 3 to 12 months. If the body absorbs the bio-compatible bulking material, it can be re-injected by a repeat of the method described. If the narrowing of the pylorus is found to be too great, the opening can be increased by the use of a balloon, which can be inserted into the pylorus and inflated to increase the opening. This flexibility in adjusting the pyloric opening to accommodate specific patent requirements provides a unique advantage over present surgical procedures.

While the injection of the bulking bio-compatible bulking material into the pyloric area will control obesity, the invention may encompass additional support procedures. For instance, the pyloric area can also be narrowed by intentionally scarring the pyloric area with either a laser or a thermal device. In such an embodiment of the invention, a laser or heating device could be placed through the biopsy channel of the endoscope and used to cauterize an area of the pylorus. In addition, in another embodiment of the invention, a sewing device could be placed through the biopsy channel of the endoscope and used to sew the pylorus and narrow the opening of the pyloric sphincter.

In yet another embodiment of the invention, gastric emptying can be further delayed by inducing a flaccid paralysis of the of the stomach. Botulinum toxin will cause a paralysis of the stomach if it is strategically injected into either the muscles of the fundus or the antrum of the stomach. Paralyzing the stomach in this way will prolong satiety by further delaying gastric emptying. The effects of botulinum toxin is expected to last for a period of 9 to 18 months.

What is claimed is:

1. A method of treating obesity comprising:
   injecting a bio-compatible bulking material submucosally or intramuscularly into the pyloric area of the stomach in an amount sufficient to cause the lumen of pylorus to narrow and slow gastric emptying;
   sewing the pylorus to narrow the lumen; and
   treating the pylorus wherein a laser or thermal device is placed through the biopsy channel and the pylorus is scarred with said device to narrow the lumen.

2. The method of claim 1, wherein said bio-compatible bulking material comprises collagen, fibrin, or elastin.

3. The method of claim 2, wherein said bio-compatible bulking material comprises collagen in one of the following forms: fibrillar, non-fibrillar, crosslinked, non-crosslinked, aqueous, or denatured gelatin.

4. The method of claim 1, wherein said bio-compatible bulking material comprises a fluoropolymer resin paste, a synthetic polymeric hydrogel, a glycoaminoglycan, a proteoglycan, or microbeads suspended in a biological fluid lubricant.

5. The method of claim 1, wherein said bio-compatible bulking material is injected through a needle inserted through a biopsy channel of an endoscope inserted into the stomach.

6. The method of claim 1, wherein a sewing device is placed through the biopsy channel and the pylorus is sewn with said device.

7. The method of claim 1, further comprising inducing supplemental flaccid paralyses of the stomach wherein a needle is placed through the biopsy channel and botulinum toxin is injected into the muscles of the fundus.

8. The method of claim 1, further comprising inducing supplemental flaccid paralyses of the stomach wherein a needle is placed through the biopsy channel and botulinum toxin is injected into the antrum of the stomach.

* * * * *